United States Patent [19]

Stekolnikov et al.

[11] 4,286,062
[45] Aug. 25, 1981

[54] PROCESS FOR PRODUCING AN ENZYME PREPARATION TO TENDERIZE MEAT PRODUCTS

[76] Inventors: Leonid I. Stekolnikov, Lipetskaya ulitsa, 26, kv. 13; Boris A. Sevastyanov, Leninsky prospekt, 36, kv. 165, both of Moscow; Gennady G. Shilov, prospekt Lenina, 121, kv. 56, Rostov-na-Donu; Anatoly A. Belousov, Sosinskaya ulitsa, 6, kv. 46, Moscow; Nikolai D. Mamonov, ulitsa Maljuginoi, 156, kv. 109, Rostov-na-Donu, all of U.S.S.R.

[21] Appl. No.: 94,325

[22] Filed: Nov. 14, 1979

[30] Foreign Application Priority Data

Nov. 22, 1978 [SU]  U.S.S.R. .............................. 2687905

[51] Int. Cl.$^3$ ............................................. C12N 9/96
[52] U.S. Cl. .................................... 435/188; 435/226; 435/816; 426/55; 426/63
[58] Field of Search ................... 426/55, 58, 59, 63; 435/188, 226, 816

[56] References Cited

U.S. PATENT DOCUMENTS

| 2,488,565 | 11/1949 | Singher et al. | 435/816 X |
| 2,676,139 | 4/1954 | Tint et al. | 435/816 X |
| 2,806,815 | 9/1957 | Singher et al. | 435/188 |
| 3,728,223 | 4/1973 | Kaneko et al. | 435/816 X |
| 3,945,889 | 3/1976 | Mima et al. | 435/816 X |
| 4,195,097 | 3/1980 | Stekolnikov et al. | 426/59 X |

FOREIGN PATENT DOCUMENTS 516977  9/1955  Canada .................................... 435/816

*Primary Examiner*—Robert A. Yoncoskie
*Attorney, Agent, or Firm*—Steinberg & Raskin

[57] ABSTRACT

An enzyme preparation for tenderizing meat products is produced from endocrine-enzyme raw stock. The testes of slaughtered cattle are comminuted and mixed with acidulated water to obtain a mixture having the pH value within the range 4.5 to 4.7, followed by isolation of an aqueous solution from said mixture, the solution containing hyaluronidase enzyme. An albumin-containing substance is then added, the ratio of albumin-containing substance to the testes being between 0.04–1.6:10–15, to obtain a suspension containing the end product. The suspension is concentrated by evaporation in vacuo at a maximum temperature of 25° C. to form a concentrate of the end product, which is then dried.

6 Claims, No Drawings

PROCESS FOR PRODUCING AN ENZYME PREPARATION TO TENDERIZE MEAT PRODUCTS

The present invention relates to processes for producing enzyme preparations for tenderizing various meat products.

The preparation finds extensive application in the meat-industry and in public catering establishments.

Known in the art are processes for producing enzyme preparations for treating meat products, viz., bromeline and bromelain from pineapple (cf. a paper by O. Silbersten, Amer. Perfumery and Aromatics, 1960, v. 75, p. 41); an enzyme preparation from germinating soyabean seeds (cf. a thesis for a Candidate's degree "Studies into protolytic enzymes of germinating soybean seeds as meat tenderizers" by A. S. Ratushny, Moscow, 1964 (in Russian); ficin from fig latex (cf. "Meat tenderization" by V. I. Solovyov, Pishchevaya promyshlennost' Publishers, Moscow, 1966 (in Russian); an enzyme preparation papain (cf. U.S. Pat. Nos. 2,961,324; 3,276,879).

The methods of preparing heretofore-known enzyme tenderizing agents are disadvantageous, in some cases, in that they require highly expensive and scarcely available original stock, and in other cases, in their instability upon prolonged storage. Moreover, some of the above-stated enzyme tenderizing agents, e.g., that obtained from germinating soybean seeds, impart a foreign odour to the meat products being tenderized, are liable to become contaminated with microflora, and produce only an insignificant effect.

One prior-art process for producing an activated enzyme proparation from the pancreas of slaughtered animals for the tenderizing of meat products consists in comminuting the defatted pancreas of slaughtered animals, then subjected the same to cutting and autolysis at 40° C. The resulting autolysate is mixed with materials that prolong or stabilize the biological life, whereupon the thus-obtained mixture is extracted with water, the grist is separated by filtration and then reextracted with water. The grist remaining after the reextraction is again separated by filtration. The filtrates are then intermixed and doped with materials that prolong or stabilize the biological life. The resultant mixture is passed through a sterilizing filter and packed in sterile containers.

The above-discussed process for producing the enzyme preparation of the character set forth hereinbefore suffers from complicated and prolonged production techniques and is disadvantageous in having an objectionable odour and featuring too short an effective biological life. In addition, the preparation is not able to adequately tenderize tough meat.

It is therefore an object of the present invention to provide a process for producing an enzyme meat tenderizing agent that is stable upon storage that provided a prolonged specific action, and that can be produced by simple production techniques.

According to the above object the invention consists in a process for producing an enzyme agent for tenderizing meat, consisting in that the testes of slaughtered cattle are used as an endocrine-enzyme original stock; the testes are comminuted and mixed with acidulated water to obtain a mixture having the pH value ranging within 4.5 to 4.7; the aqueous solution is isolated from the mixture, said solution containing enzyme hyaluronidase; an albumin-containing substance is added to the solution in a ratio of the albumin-containing substance to the testes of of about 0.04–1.6:10–15, thus obtaining a suspension containing the end product, whereupon the above suspension is concentrated by evaporation at a maximum temperature of 25° C. to form a concentrate of the end product, which is then dried.

It is recommended that, with a view to producing the end product of a higher degree of purity, the above-mentioned concentrate be subjected, prior to drying, to filtration or separation.

The concentrate of the end product is most expediently freeze dried in a layer whose thickness ranges within 2 to 12 mm.

It is recommended that blood serum be used as an albumin-containing substance, with a weight ratio of blood serum to testes ranging from 0.8–1.6:10–15. Also recommended for use is clear food albumin, with a weight ratio of clear food albumin to testes ranging from 0.04–0.08:10–15.

The resultant preparation is essentially a complex of enzyme hyaluronidase and albumin-containing substance, and is in fact a free-flowing powder coloured from light-brown to pinkish-brown, possessing only a faint specific odour which disappears upon tenderizing meat products with the preparation. Maximum moisture content of the preparation is 5 weight percent. The preparation is soluble in water and in pickle solutions, the pH of a 0.1-percent aqueous solution of the preparation being equal to 6 or 7. The hyaluronidase potency of the preparation ranges within 100 to 128 arbitrary units per 100 mg. A maximum total amount of microorganisms is 1000 per gram. The preparation is non-toxic when used over a prolonged period of time.

The preparation contains a negligible amount of impurities which produce no adverse affect on the enzyme properties, though these impurities somewhat reduce the hyaluronidase potency of the preparation.

An albumin-containing substance "per se" features no enzymic activity and therefore produces no effect upon the quality of meat products. However, the addition thereof to the enzyme, viz., hyaluronidase according to the present invention due to the fact that albumin is a macromolecular protein having a molecular weight of about 65000, and contains such reactive groups in its molecule as —$NH_2$, —COOH, and others, results in an interaction thereof with hyaluronidase to form a complex compound, wherein the active labile centres of the enzyme are protected against the destructive environmental factors (e.g. light, moisture, etc.). This in turn results in the specific hyaluronidase activity of the resulting agent remaining over a longer period of time then in the case of the enzyme itself.

Meat and meat products are treated with the thus-obtained preparation by the dry or wet method, in an amount of 0.05 to 0.2 percent of the meat weight, or by injecting a solution of the preparation.

As early as 3 to 6 hours after treatment, a pronounced increase (by 15 to 20 percent) in the moisture-retaining capacity and in tenderness of the treated specimens is observed as compared to untreated meat; there are noted accumulation of free aminoacids and microstructure modifications in the muscular tissue, which is indicative of accelerated biochemical meat tenderization processes. When ageing meat or meat products not enzyme-tenderized, at +2° C. the characteristics approximating the above-stated characteristics are attained as late as after 10 to 12 days, i.e., the meat ageing processes proceed 10 to 12 times faster with the use of the enzyme preparation of the invention.

Application of the enzyme preparation produced by the process disclosed in the present invention for tenderizing meat products features a number of advantages over the use of other enzyme preparations for the same purpose.

The preparation disclosed herein is stable upon prolonged storage and retains its potency over a two-year period when exposed to a temperature of +18to +20° C. In addition, the preparation exhibits a specific ability to decompose hyaluronic acid which constitutes part of the connective tissue and also activates natural proteinases of muscular tissue, which in turn hydrolyze actomyosin and some other muscular proteins. This leads eventually to a higher rate of meat digestion and to its increased biological value.

The process for producing an enzyme preparation is simple as to production process techniques and is carried into effect preferably in the following way.

Testes of slaughtered animals are comminuted in a mincer, whereupon the resultant mincemeat is covered over with acidulated water, e.g., with an aqueous acetic acid solution so that the pH value of the obtained mixture is between 4.5 to 4.7. Then an aqueous solution is isolated from the resultant mixture, the solution containing enzyme hyaluronidase, whereupon an albumin-containing substance is added to the solution, and the solution is thoroughly stirred to obtain a suspension. The thus-obtained suspension is concentrated by evaporation in vacuo at a maximum temperature of 25° C., while in some cases the suspension is preliminarily filtered.

As a result, a concentrate of the end product is obtained, which is then dried. The end-product containing concentrate can be dried by any of the known methods, viz., by spraying or freezing, the latter method being preferable. To carry the freezedrying into effect, the concentrate is poured into trays in a layer 2 to 12 mm deep, whereupon the trays are put in freezing chambers at −40° to −60° C. Then the frozen product is transferred to a vacuum freeze drier to be dried at a temperature gradually rising to +25°−+30° C. The product is allowed to stand at that temperature for at least six hours until the end product is obtained with a maximum residual moisture content of 5 percent.

In order to produce an enzyme preparation featuring a higher purity, the mass is either filtered or separated prior to drying.

For better understanding of the present invention some practical embodiments thereof are given below by way of example.

EXAMPLE 1

Testes of slaughtered animals (100 kg) are disintegrated in a mincer having holes 2 mm in diameter. The resultant mincemeat is poured over with 200 l water acidulated with a 0.1 N acetic acid solution to bring the pH of the thus-obtained mixture to 4.5.

Then an aqueous solution, containing enzyme hyaluronidase is isolated from the mixture. 9 l of blood serum are added to 190 l of the aqueous solution, whereupon the mixture is carefully stirred for an hour. The result is a suspension, from which the end product is isolated. To this end, the suspension is first filtered, and the filtrate is concentrated by evaporation in vacuo at 25° C. to obtain 20 l of a concentrate of the end product which is then passed through folded paper filters.

The filtered solution is dispensed to trays in a layer 2 mm thick, allowed to stand at −40° C. for six hours, and put in a vacuum freeze drier, whereupon the temperature in the latter is raised gradually to +25° C. The product is kept for six hours to obtain 3.25 kg of the end product having a residual moisture content of 3.5 percent, which is then packed in containers.

When manufacturing sausage products, such as smoked sausage, the enzyme preparation is introduced into the stock in the course of mixing with the curing ingredients, in an amount of 100 g per 100 kg of stock. For better distribution of the preparation in the mincemeat it is expedient to introduce the preparation into the stock as a 10 to 20 percent aqueous solution. Thereupon the sausage mince is prepared according to the formulation and then filled in the skin. Next the filled casings are allowed to set at 2° to 6° C. and high relative humidity (90 to 98 percent) for 1 to 3 days, whereupon the sausage loaves are subjected to fume smoking at a temperature of from 12° to 22° C. for 2 to 4 days. After that the sausage loaves are drived at a maximum temperature of 15° C., preferably 12° C. while strictly adjusting the relative humidity so that it should be somewhat higher at the beginning of the drying process and should be decreased gradually towards the end of that process. It is preferred that the relative humidity percentage be about 80 at the beginning of the drying, and about 75 at the end. The duration of the drying period is 20 to 35 days depending upon the loaf diameter and kind of sausage.

Sausage products manufactured according to the above-specified techniques feature dense consistency and markedly pronounced smoked flavour.

EXAMPLE 2

The process is carried out as in Example 1 with the exception that the pH value of the mixture of the testes of slaughtered animals with acidulated water is 4.7, and the resultant concentrate is immediately subjected to freeze drying at −60° C. within 4 hours, with the depth of the concentrate layer dispensed to a tray equal to 2 mm. The result is the end product in an amount of 4.1 kg. The thus-obtained enzyme preparation features the properties similar to those described in Example 1, though the product yielded contains some negligible amount of impurities.

EXAMPLE 3

The process is carried out as in Example 1 with the exception that as the albumin-containing substance a clear 3-percent solution of food albumin is used in an amount of 15 l, while the final drying temperature is 30°.

The thus-obtained enzyme preparation exhibits properties similar to those of Example 1.

EXAMPLE 4

The process is carried out as in Example 3, with the exception that the testes of slaughtered animals (100 kg) and a clear 3-percent solution of food albumin (13.3 l) are used, whereas the end product concentrate is dispensed to trays in a layer 8 mm deep for freeze-drying. The thus-obtained enzyme preparation has properties similar to those of Example 1.

EXAMPLE 5

The process is carried out as in Example 1, with the exception that the testes of slaughtered animals (130 kg) and blood serum (16 l) are used, the layer of the end product concentrate when dispensed for freeze-drying is 5 mm, and the final drying temperature is 27° C. The thus-obtained enzyme preparation has properties similar to those of Example 1.

EXAMPLE 6

The process is carried out as in Example 1, with the exception that the testes of slaughtered animals (150 kg) and blood serum (10 l) are used, and the freezing temperature of the end product concentrate equals −50° C. The thus-obtained enzyme preparation has properties similar to those of Example 1.

EXAMPLE 7

The process is carried out as in Example 1, with the exception that the testes of slaughtered animals (130 kg) and a clear 3-percent solution of food albumin (20 l) are used, and the end product concentrate is dehydrated by spraying.

The thus-obtained enzyme preparation exhibits properties similar to those of Example 1.

What is claimed is:

1. Method of producing an enzyme meat tenderizing agent, which comprises comminuting the testes of slaughtered animals, extracting the thus-comminuted testes with acidudated water of a pH and in an amount sufficient to obtain a mixture having a pH value of 4.5–4.7, separating an aqueous solution from the thus obtained mixture, said aqueous solution containing hyaluronidase, adding an albumin-containing substance to said aqueous solution in an amount such that the ratio of said albumin-containing substance to the testes of the slaughtered animals is between about 0.04–1.6:10–15, thus forming a suspension, subjecting the thus-formed suspension to concentration by evaporation at a maximum temperature of 25° C., thus obtaining a concentrate of the enzyme meat tenderizing agent, and drying the thus obtained concentrate.

2. The process of claim 1, wherein said concentrate is subjected to filtration prior to being dried.

3. The process of claim 1, wherein said concentrate is subjected to separation from suspended material prior to being dried.

4. The process of claim 1, wherein blood serum is used as the albumin-containing substance, the ratio of blood serum to the testes being between 0.8–1.6:10–15.

5. The process of claim 1, wherein a clear aqueous solution of food albumin is used as the albumin-containing substance, the ratio of said food albumin to the testes being between 0.04–0.08:10–15.

6. The process of claim 1, wherein the concentrate is freeze-dried, with the layer of said concentrate being 2 to 12 mm deep.

* * * * *